US00PP13848P29

(12) United States Plant Patent
Unger

(10) Patent No.: US PP13,848 P2
(45) Date of Patent: May 27, 2003

(54) PLECTRANTHUS PLANT NAMED 'NICOLLETA'

(75) Inventor: Michael H. Unger, Rheinfelden (DE)

(73) Assignee: Unger Breeding (DE)

( * ) Notice: Subject to any disclaimer, the term of this patent is extended or adjusted under 35 U.S.C. 154(b) by 0 days.

(21) Appl. No.: 10/113,090

(22) Filed: Apr. 1, 2002

(51) Int. Cl.[7] ..... A01H 5/00

(52) U.S. Cl. ..... Plt./373

(58) Field of Search ..... Plt./373

(56) References Cited

PUBLICATIONS

Andrew Hankey, Plectranthus, Witwatersand National Botanical Garden, South Africa, Apr. 2001.*
http://www.salisburygreenhouse.com/annuals.htm.*

* cited by examiner

*Primary Examiner*—Bruce R. Campell
*Assistant Examiner*—W C Haas
(74) *Attorney, Agent, or Firm*—Wood, Phillips, Katz, Clark & Mortimer

(57) ABSTRACT

A new and distinct cultivar of Plectranthus plant named 'Nicolleta', characterized by its upright mounded and trailing form, sericeous gray-green foliage and vigorous growth habit.

2 Drawing Sheets

LATIN NAME OF THE GENUS AND SPECIES OF PLANT CLAIMED

*Plectranthus argentatus.*

VARIETY DENOMINATION

Nicolleta.

BACKGROUND OF INVENTION

The present invention comprises a new and distinct Plectranthus plant, hereinafter referred to by the cultivar name 'Nicolleta'. The new cultivar was discovered as a mutation of an unnamed *Plectranthus argentatus* selection (not patented) in Rheinfelden, Germany in 1998.

Asexual reproduction of the new cultivar by terminal or stem cuttings taken during 2000–2001 at West Chicago Ill. has demonstrated that the characteristics of the new cultivar as herein described are firmly fixed and retained through successive generations of such asexual propagation.

SUMMARY OF THE INVENTION

It was found that the cultivar of the present invention:

(a) Exhibits a trailing form;
(b) Forms sericeous gray-green foliage; and
(c) Exhibits a vigorous growth habit.

'Nicolleta' has not been observed under all possible environmental conditions to date. Accordingly, it is possible that the phenotype may vary somewhat with variations in the environment, such as temperature, light intensity, and day length.

When the new cultivar of the present invention is compared to the Plectranthus variety 'Variegata' (not patented) the new cultivar is more compact and upright and has solid green foliage color, whereas 'Variegata' has green and cream variegated foliage.

BRIEF DESCRIPTION OF PHOTOGRAPHS

The accompanying photographs show as nearly true as it is reasonably possible to make the same in color illustrations of this type, typical flower and foliage characteristics of the new cultivar. The plants were grown in a greenhouse at West Chicago, Ill., USA.

The first photograph illustrates the general growth habit of the new cultivar.

The second photograph illustrates a close up of the leaves of the new cultivar.

DETAILED BOTANICAL DESCRIPTION

The chart used in the identification of colors described herein is The R.H.S Colour Chart of The Royal Horticultural Society, London, England. The color values were determined on Jul. 27, 2001 in West Chicago, Ill. The readings were taken between 10:00 and 11:45 p.m. under natural light conditions. The plants were produced from cuttings taken from stock plants and were grown for 12 weeks under greenhouse conditions comparable to those used in commercial practice. A soilless growth medium was utilized and temperatures of approximately 75° to 80° F. (24° to 26° C.) during the day and approximately 58° to 65° F. (14° to 18°C.) during the night and light levels of between 4,000 and 7,000 foot candles were maintained. Plants used for the following descriptions and measurements were grown for twleve (12) weeks from rooted cuttings.

Botanical classification: *Plectranthus argentatus* cultivar 'Nicolleta'.

Propagation:
- *Type cutting.*—Terminal tip.
- *Time to form roots.*—Approximately 21–28 days.

Plant description:
- *Crop time.*—Six to eight weeks in a 20 cm pot.
- *General appearance and form.*—Upright bushy shrub.
- *Plant height.*—Approximately 9.4 cm.
- *Plant spread.*—Approximately 60 cm.

*Number of branches.*—Average of 8 main branches with approximately 15 leaves per branch.

*Branch.*—Length: Approximately 55.1 cm. Diameter: Approximately 4 mm. Color: 138C with overlay of 183A. Texture: Densely covered with soft hairs.

*Internode length.*—At third node from tip: Approximately 5.8 cm.

Foliage description:

*Form.*—Simple.

*Shape.*—Ovate.

*Margin.*—Lobulate.

*Apex.*—Acute.

*Base.*—Rounded.

*Arrangement.*—Opposite.

*Venation pattern.*—Reticulate.

*Surface.*—Appearance: Velvety. Texture: Upper surface: Sericeous.

*Color of young and mature foliage.*—Upper surface: 138A. Lower surface: 138B. Venation pattern: Reticulate. Venation color: 138C. Size — Approximately 4.6 cm in length and approximately 3.9 cm in width.

*Petiole.*—Length: Approximately 2 cm. Diameter: Approximately 2 mm. Color: 138C. Texture: Densely covered with soft hairs.

Flower description: Flower production was not observed.

Seed production: Seed production was not observed.

Disease resistance: Disease resistance has not been observed.

I claim:

1. A new and distinct cultivar of Plectranthus plant named 'Nicolleta' substantially as herein shown and described, which:

(a) Exhibits an upright mounded and trailing form;

(b) A vigorous growth habit; and (c) Sericeous gray-green foliage.

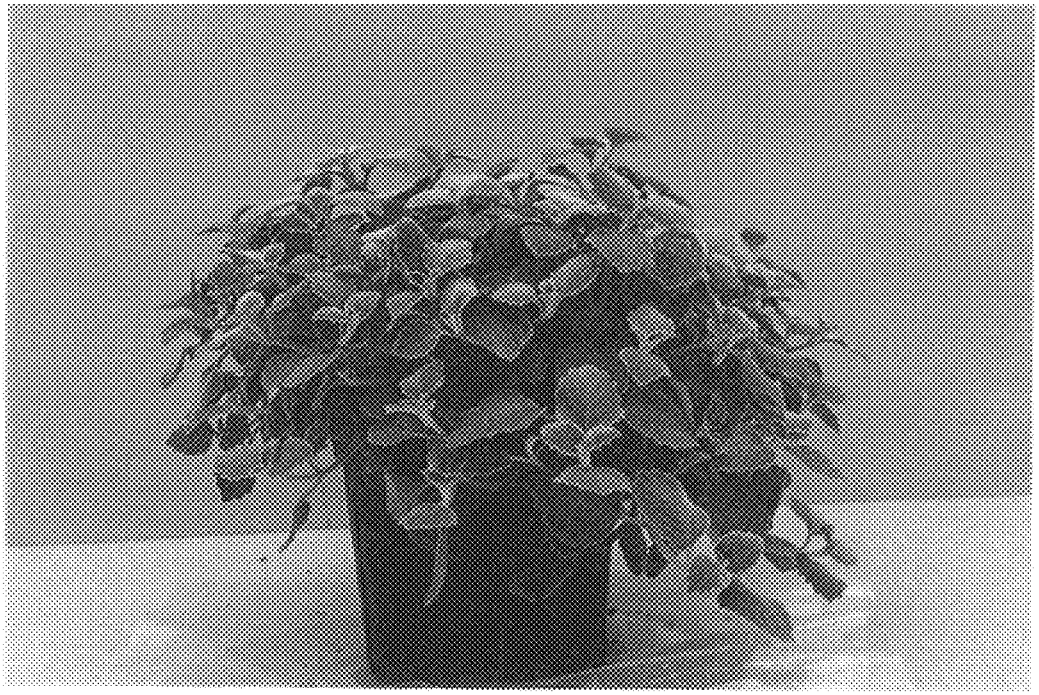

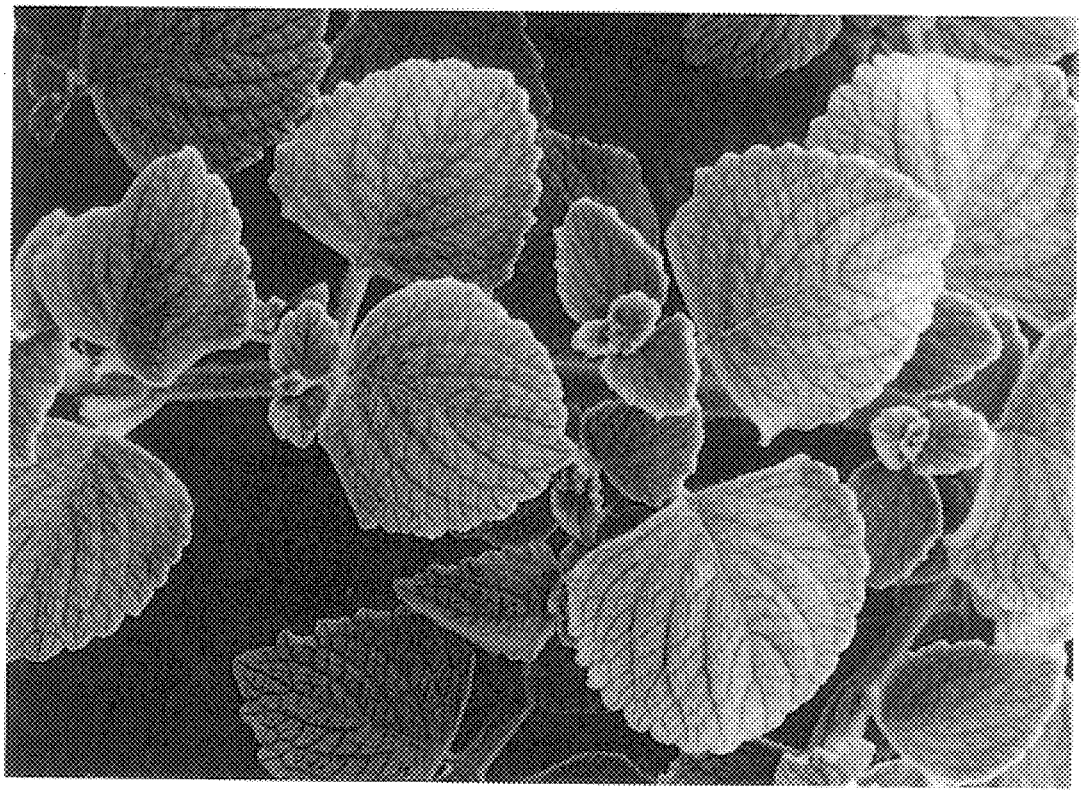

* * * * *